United States Patent
Rech et al.

(10) Patent No.: US 12,383,493 B2
(45) Date of Patent: *Aug. 12, 2025

(54) DRUG DELIVERY FORMULATIONS

(71) Applicant: MedinCell S.A., Jacou (FR)

(72) Inventors: Anthony Rech, Saint Aunès (FR); Christophe Roberge, Le Crès (FR); Eran Harary, Netanya (IL)

(73) Assignee: MEDINCELL S.A., Jacou (FR)

(*) Notice: Subject to any disclaimer, the term of this patent is extended or adjusted under 35 U.S.C. 154(b) by 361 days.

This patent is subject to a terminal disclaimer.

(21) Appl. No.: 17/642,410

(22) PCT Filed: Sep. 11, 2020

(86) PCT No.: PCT/IB2020/058474
§ 371 (c)(1),
(2) Date: Mar. 11, 2022

(87) PCT Pub. No.: WO2021/048817
PCT Pub. Date: Mar. 18, 2021

(65) Prior Publication Data
US 2022/0331240 A1  Oct. 20, 2022

Related U.S. Application Data

(60) Provisional application No. 62/900,061, filed on Sep. 13, 2019.

(51) Int. Cl.
| | |
|---|---|
| A61K 9/00 | (2006.01) |
| A61K 31/519 | (2006.01) |
| A61K 47/20 | (2006.01) |
| A61K 47/34 | (2017.01) |
| A61P 25/18 | (2006.01) |

(52) U.S. Cl.
CPC .......... *A61K 9/0024* (2013.01); *A61K 31/519* (2013.01); *A61K 47/20* (2013.01); *A61K 47/34* (2013.01); *A61P 25/18* (2018.01)

(58) Field of Classification Search
CPC ...... A61K 31/519; A61K 47/20; A61K 47/34; A61K 9/0024; A61P 25/18
See application file for complete search history.

(56) References Cited

U.S. PATENT DOCUMENTS

| | | | |
|---|---|---|---|
| 9,023,897 B2 | 5/2015 | Gaudriault | |
| 9,737,605 B2* | 8/2017 | Wright | A61M 5/2033 |
| 2005/0026133 A1 | 2/2005 | Nakatsuji et al. | |
| 2012/0172454 A1 | 7/2012 | Gaudriault | |
| 2016/0030337 A1 | 2/2016 | Kuzma et al. | |
| 2019/0160171 A1 | 5/2019 | Gaudriault et al. | |
| 2019/0255179 A1 | 8/2019 | Wright et al. | |
| 2023/0135427 A1 | 5/2023 | Dadey et al. | |

FOREIGN PATENT DOCUMENTS

| | | | |
|---|---|---|---|
| CN | 101584652 A | 11/2009 | |
| CN | 103491946 A | 1/2014 | |
| CN | 104582733 A | 4/2015 | |
| CN | 105163719 A | 12/2015 | |
| CN | 111107840 A | 5/2020 | |
| JP | 2010-531807 A | 9/2010 | |
| JP | 2012-504146 A | 2/2012 | |
| WO | WO 99/07343 A1 | 2/1999 | |
| WO | WO 03/064634 A1 | 8/2003 | |
| WO | WO 2012/090070 A2 | 7/2012 | |
| WO | WO-2013063125 A1 * | 5/2013 | ........... A61K 9/0024 |
| WO | WO-2014001904 A1 * | 1/2014 | ........... A61K 31/445 |
| WO | WO 2014/164754 A1 | 10/2014 | |
| WO | WO 2019/016233 A1 | 1/2019 | |

OTHER PUBLICATIONS

International Search Report, issued in PCT/IB2020/058474, dated Dec. 2, 2020.
Written Opinion of the International Searching Authority, issued in PCT/IB2020/058474, dated Dec. 2, 2020.
Al-Tahami et al., "Smart Polymer Based Delivery Systems for Peptides and Proteins," Recent Patents on Drug Delivery & Formulation, vol. 1, 2007, pp. 65-71 (8 pages total).
Andreasen et al., "Remission in Schizophrenia: Proposed Criteria and Rationale for Consensus," Am J Psychiatry, vol. 162, No. 3, Mar. 2005, pp. 441-449.
Cilurzo et al., "Injectability Evaluation: An Open Issue," AAPS PharmSciTech, 2011 (Published online May 7, 2011), 7 pages total.
Japanese Office Action for Japanese Application No. 2022-516406, dated Aug. 20, 2024, with English translation.
Japanese Search Report for Japanese Application No. 2022-516406, dated Aug. 23, 2024, with English translation.
Spis et al., "Biocompatibility of MedinGel biodegradable drug delivery system in the eye," ARVO Annual Meeting Abstract, vol. 55, 5273, Apr. 2014, 2 pages total.
Chinese Office Action and Search Report for Chinese Application No. 202080077874.0, dated Jun. 10, 2023, with an English translation.

* cited by examiner

*Primary Examiner* — Sarah Pihonak
(74) *Attorney, Agent, or Firm* — Birch, Stewart, Kolasch & Birch, LLP

(57) ABSTRACT

The present invention is directed to methods of treating psychiatric diseases and disorders comprising administering to a subject in need thereof an injectable formulation comprising risperidone, triblock and diblock copolymers wherein the concentration of the risperidone is 250-400 mg/mL and injection volume is 1 mL or less.

30 Claims, 2 Drawing Sheets

DRUG DELIVERY FORMULATIONS

CROSS REFERENCE TO RELATED APPLICATION

This application is the National Phase of PCT International Application No. PCT/IB2020/058474, filed on Sep. 11, 2020, which claims priority under 35 U.S.C. 119(e) to U.S. Provisional Application No. 62/900,061, filed on Sep. 13, 2019, all of which are hereby expressly incorporated by reference into the present application.

FIELD OF THE INVENTION

The present invention relates to methods of treating psychiatric diseases and disorders responsive to risperidone with high-concentration, low-volume risperidone pharmaceutical compositions comprising a triblock copolymer and a diblock copolymer.

BACKGROUND OF THE PRESENT INVENTION

Risperidone is an atypical antipsychotic, a serotoninergic (5-HT2A receptor) and dopaminergic (D2, D3 and D4 receptor) antagonist. The substance also binds to alpha-1-adrenergic receptors, histaminergic H1 receptors and, to a lesser extent, alpha-2-adrenergic receptors. It does not have affinity for cholinergic receptors. Risperidone has been approved by the FDA since 1994 for the treatment of schizophrenia in adults and adolescents aged 13 to 17, and has been marketed under the name Risperdal®. Currently available in oral and injectable versions, risperidone is approved for a number of other indications, including treatment for dementia, anxiety, some bipolar disorders, depression, and manic or psychotic episodes.

Risperidone is used in first-line treatment of schizophrenia due to its safety profile and recommendation for medium and long-term treatment. Long acting injectable (LAI) products have been approved by the FDA. Risperdal Consta®, is an injectable risperidone product for biweekly intramuscular (IM) administration. Risperdal Consta is provided at doses 12.5 mg, 25 mg, 37.5 mg, and 50 mg risperidone/vial with a syringe having 2 mL of diluent. The product requires multiple reconstitution steps and oral supplementation at the start of treatment. Intramuscular injections are typically painful and anxiety inducing, in particular to the target population. Perseris®, an injectable risperidone product for monthly subcutaneous administration, is provided in two syringes which require significant mixing and resuspension prior to administration. Perseris® is provided in two dose strengths, 90 mg (0.6 mL) and 120 mg (0.8 mL).

Drug delivery systems including polymers such as diblock and triblock copolymers have been used to deliver a variety of drugs and are generally formulated to deliver specific drugs whether they are hydrophobic drugs or hydrophilic drugs. Depending on the drug solubility, these drug formulations differ in polymer concentrations, types of polymers utilized, molecular weights of the polymers and solvents used in the formulations.

The type of environment in which the drug is delivered is an important consideration in formulating a drug delivery system. Thus, there exist drug delivery compositions that are prepared using temperature sensitive polymers, phase sensitive polymers, pH sensitive polymers and photosensitive polymers. See, for example, K. Al-Tahami and J. Singh "Smart Polymer Based Delivery Systems for Peptide and Proteins," Recent Patents on Drug Delivery & Formulation, 1: pages: 65-71 Bentham Science Publishers, LTD. 2007.

U.S. Pat. No. 9,023,897 and US patent publication US2019/160171 describe pharmaceutical formulations made of biodegradable triblock and diblock polymers, which are useful for the delivery of a variety of actives.

There is a need for long-acting risperidone formulations that support patient compliance, lessen patient administration anxiety, and are easier for health care professionals to prepare and administer. A challenge in treating psychiatric diseases or disorders using risperidone include, for example, the ability to subcutaneously inject a long-acting formulation having a high dose of active agent in a low injection volume, with an injectable viscosity. Another challenge is the development of a long-acting, subcutaneous injectable formulation having a low initial burst of active agent. In the event the long-acting formulation must be removed (due to an adverse event or other reason), the long-active formulation must be excisable from the patient. The methods disclosed herein meet those needs and others.

SUMMARY OF THE INVENTION

Provided herein are methods of treating a psychiatric disease or disorder in a subject, comprising subcutaneously administering to the subject with a frequency of no more than once every 21 days:
  1 mL or less of a pharmaceutical formulation comprising:
    a) risperidone, or a pharmaceutically acceptable salt thereof, at a concentration of about 250-400 mg/mL, equivalent to risperidone;
    b) a biodegradable triblock copolymer having the formula:

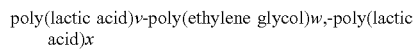

poly(lactic acid)$v$-poly(ethylene glycol)$w$,-poly(lactic acid)$x$ wherein v and x are the number of repeat units ranging from 24 to 682 and w is the number of repeat units ranging from 4 to 273 and v=x or v≠x;
    c) a biodegradable diblock copolymer having the formula:

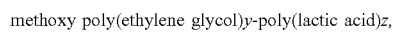

methoxy poly(ethylene glycol)$y$-poly(lactic acid)$z$, wherein y and z are the number of repeat units, wherein y is the number of repeat units ranging from 3 to 45 and z is the number of repeat units ranging from 7 to 327; and
  wherein the ratio of the biodegradable triblock copolymer of (b) and the biodegradable diblock copolymer of (c) is 1:3 to 1:8 or 1:1 to 1:19 or 3:2 to 1:19, in said formulation, which is insoluble in an aqueous environment.

In particular, the active principle of the injectable formulation of the present invention is risperidone present in a concentration of 250 mg/mL or greater, for example, about 250 mg/mL to 400 mg/mL, or about 300 mg/mL to about 400 mg/mL or a pharmaceutically acceptable salt thereof in an amount equivalent to 250 mg/mL to 400 mg/mL risperidone.

With the injectable formulations of the invention, the active principle has a release duration of 21-90 days (about 3 weeks to about 3 months) or 30-90 days (about 1 month to about 3 months). In some aspect, the release duration is about 28-31 days (about 4 weeks to about 1 month). In some aspect, the release duration is about 56-63 days (about 8 weeks to about 2 months to about 9 weeks). In some aspects, the release duration is about 84-94 days (about 12 weeks to about 13 weeks or about 12 weeks to about 3 months).

Other aspects and embodiments are set forth below, or will readily arise from the following description of the preferred embodiments.

DETAILED DESCRIPTION OF THE INVENTION

Definitions

Figure 1:
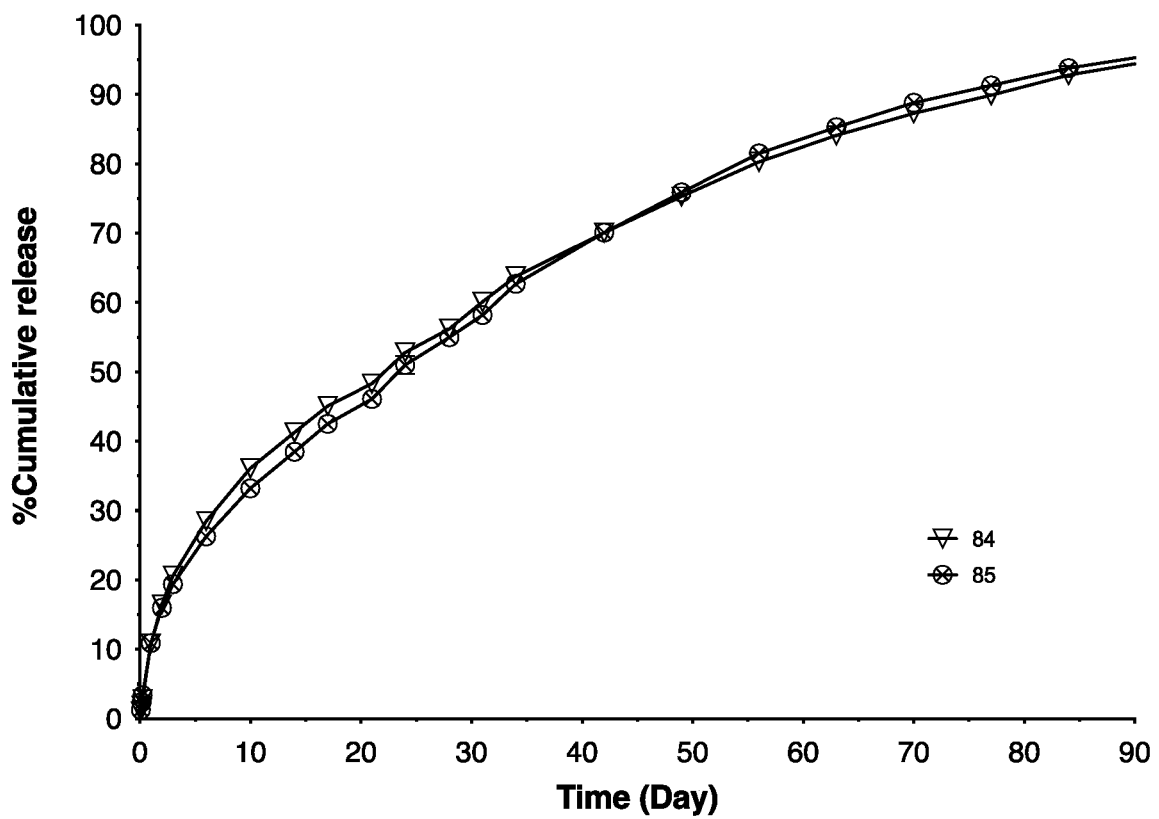
FIG. 1 shows % Cumulative release as a function of time for Formulations F84 and F85.
Figure 2:
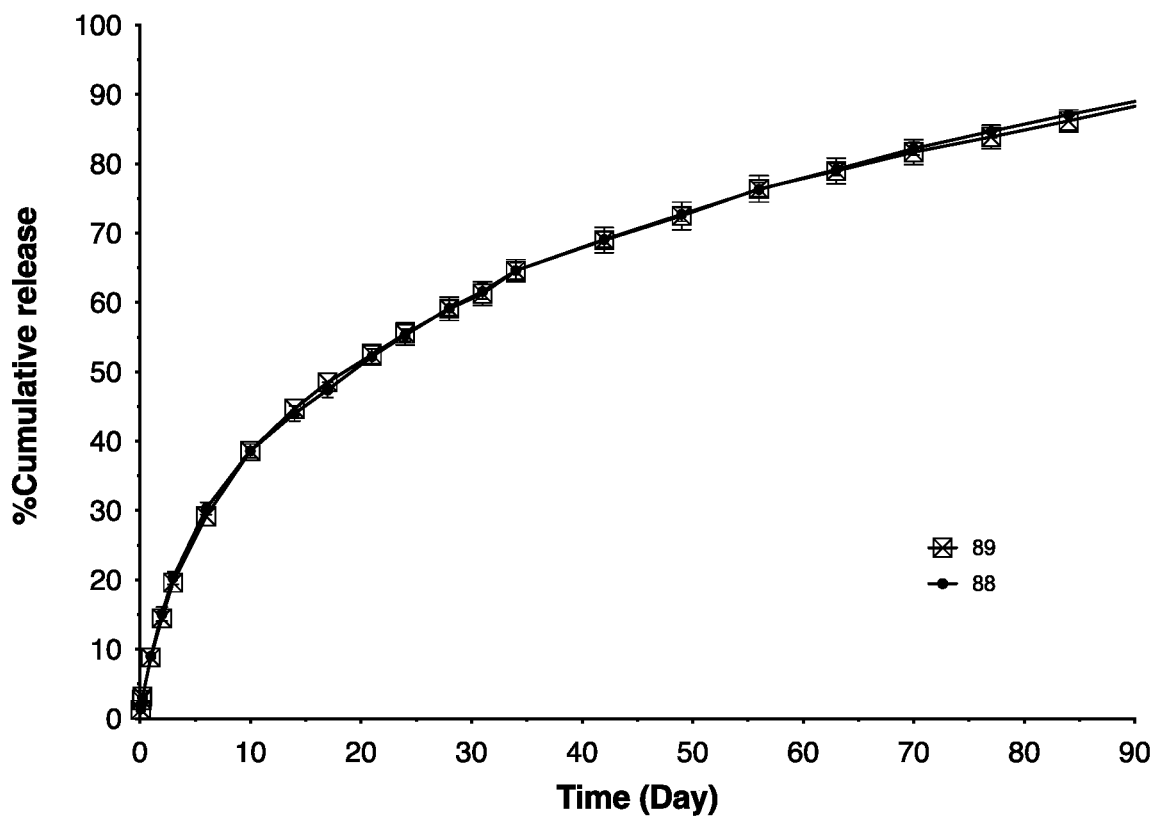
FIG. 2 shows % Cumulative release as a function of time for Formulations F88 and F89.

As used herein the term "biodegradable" means that the triblock and diblock copolymers will after a period of time erode or degrade in vivo to form smaller non-toxic components.

The term "parental administration" encompasses intramuscular, intraperitoneal, intra-abdominal, subcutaneous, intravenous and intraarterial. It also encompasses intradermal, intracavernous, intravitreal, intracerebral, intrathecal, epidural and intraosseous administration. In some embodiments, administration is subcutaneous.

The term "about" should be considered as disclosing the range defined by the absolute values of the two endpoints. For example, the expression "from about 300 to about 400" also discloses the values 300 and 400. When used to modify a single number, the term "about" may refer to plus or minus 10% of the indicated value and includes the indicated number. For example, "about 15%" may indicate a range of 13.5% to 16.5%, and "about 1" means from 0.9 to 1.1.

The term "subject" encompasses all members of the Kingdom Animalia.

The active principle according to the invention is risperidone and pharmaceutically acceptable salts thereof.

As used herein, "psychiatric disease or disorder" refers to a mental illness, regardless of etiology. Certain psychiatric diseases and disorders known to be responsive to risperidone include, for example, schizophrenia, schizoaffective disorder, bipolar disorder, and irritability in children on the autism spectrum.

The term "implant" means that the drug delivery compositions are injectable, are in situ forming, are biodegradable and turn into solid (or semi solid) implants in situ. Thus, the formulations that are disclosed herein are flowable liquids that can be easily injected through a syringe without excessive force.

As used herein "repeat units" are the fundamental recurring units of a polymer. For example, lactic acid (LA) is the repeat unit in poly(lactic acid) and ethylene oxide (EO) is the repeat unit in poly(ethylene glycol).

By "end-capped polyethylene glycol" (cPEG) refers to PEG's in which one terminal hydroxyl group is reacted and includes alkoxy-capped PEG's, urethane-capped PEG's ester-capped PEG's and like compounds. The capping group is a chemical group which does not contain a chemical function susceptible to react with cyclic esters like lactide, glycolide, caprolactone and the like or other esters and mixtures thereof. The reaction of an end-capped PEG polymer with lactide generates a diblock cPEG-PLA copolymer. For example, mPEG-PLA refers to a methoxy capped PEG-polylactide diblock copolymer.

The abbreviation "PEG" refers to poly(ethylene glycol), poly(ethylene oxide) or poly(oxyethylene) and the terms are used interchangeably herein.

The abbreviation of "PLA" refers to polylactide, polylactic acid or poly(lactic acid) and the terms are used interchangeably herein.

The abbreviation "T" or "TB" refers to a triblock copolymer(s), while the abbreviation "D" or "DB" refers to a diblock copolymer(s).

The term "diblock" as used herein refers, for example, to an end-capped PEG-polyester copolymer. "mPEG" refers to methoxy polyethylene glycol. The PEG in the diblock copolymer may be capped with known capping entities other than a methoxy group. Examples of end-capped polyethylene glycols include alkoxy capped PEG's such as methoxyPEG or ethoxyPEG, urethane-capped PEG's, ester-capped PEG's, amine-capped PEG's and amide-capped PEG's.

This list of end-capped PEG's is not exhaustive and a person skilled in the art would recognize additional end-capped PEG's, which are not listed.

The term "triblock" refers, for example, to a polyester-PEG-polyester copolymer, preferably poly(lactic acid)-PEG-poly(lactic acid) copolymer.

The biodegradable drug delivery compositions used in the methods of the present invention are described in U.S. Pat. No. 9,023,897, the entirety of which is incorporated by reference herein.

The structure of the biodegradable triblock/diblock copolymers of the invention may also be represented as follows:

Av-Bw-Ax, which refers to the triblock copolymer poly (lactic acid)v-poly(ethylene oxide)w-poly(lactic acid)x, is also identified herein as PaRb, where "a" is the PEG size in kDa and "b" is the molar ratio LA/EO (v+x/w).

Cy-Az, which refers to the diblock mPEG-PLA copolymer: methoxy-poly(ethylene glycol)y-poly(lactic acid)z, is also identified herein as dPaRb, where "a" is the PEG size in kDa and "b" is the molar ratio LA/EO (z/y). The methoxy group, or other capping group, will cap one of the two hydroxyl groups of the PEG. The poly(lactic acid) chain will extend only from the free hydroxyl group.

The number of repeat units (degree of polymerization (DP)) of y and z in the diblock composition may vary. Thus, y can, for example, range from 7 to 43 or 3 to 45 and z can range from 32 to 123 or 7 to 327. For example, y can be 25 and z can be 123, y can be 34.5 and z can be 123 or y can be 45 and z can be 32. The degree of polymerization for PEG (DP-PEG) is calculated by dividing the PEG molecular weight of the capped PEG by the EO unit molecular weight (44 Da). The degree of polymerization for PLA (DP-PLA) is calculated by multiplying DP-PEG by the LA/EO ratio.

The LA/EO ratio refers to the molar ratio of lactic acid units to ethylene oxide units that is present in each of the block copolymers present in the biodegradable drug delivery composition. It is determined experimentally by NMR. The LA/EO molar ratio of the triblock copolymer can range from 0.5 to 3.5. In another aspect the LA/EO molar ratio in the triblock can range from 0.5 to 2.5 in the pharmaceutical formulations described herein. In yet another aspect the LA/EO ratio in the triblock can range from 0.5 to 22.3.

The LA/EO ratio in the diblock can range from 2 to 6. In another aspect the LA/EO ratio in the diblock can range from 3 to 5 in the pharmaceutical formulations described herein. In another aspect the LA/EO ratio in the diblock can range from 0.8 to 13.

The degree of polymerization or DP is the number of repeat units in an average polymer chain at time t in a polymerization reaction. For example, the degree of polymerization for PEG is about 45 to 170 or it can be 4 to 273 or 3 to 45, while for PLA it can range from about 84 to 327 or it can be 24 to 682 or 7 to 327.

The methods of the present invention use a biodegradable drug composition comprising a triblock copolymer and a diblock copolymer. The biodegradable triblock copolymer has the formula: $A_v\text{-}B_w\text{-}A_x$, wherein A is a poly(lactic acid) and B is poly(ethylene glycol) and v and x are the number of repeat units of the poly(lactic acid) and range from 24 to 682; and w is the degree of polymerization (number of repeat units) for the poly(ethylene glycol) and ranges from 4 to 273, and v=x or v≠x. The degree of polymerization for DP-PEG is calculated by dividing the PEG molecular weight by the EO unit molecular weight (44 Da). v+x equals the degree of polymerization (number of repeat units) for PLA. DP-PLA is calculated by multiplying DP-PEG by the LA/EO ratio.

The size of the PEG in the triblock copolymer can range from 194 Da to 12,000 Da.

The triblock copolymer may be combined with a biodegradable diblock copolymer having the formula: $C_y\text{-}A_z$, wherein A is a polyester (i.e., PLA) and C is an end-capped polyethylene glycol and y and z are the number of repeat units ranging from 7 to 371 or from 3 to 327. This combination has a ratio of triblock copolymer to diblock copolymer ranging from 1:3 to 1:8 or 1:1 to 1:19 or 3:2 to 1:19. In some aspects, the ratio of triblock copolymer to diblock copolymer is 3:2 to 1:5. In some aspects, the ratio of triblock copolymer to diblock copolymer is 3:2 to 1:4.5. In some aspects, the ratio of triblock copolymer to diblock copolymer is 3:2 to 1:4. In some aspects, the ratio of triblock copolymer to diblock copolymer is 3:2 to 1:3.5. In some aspects, the ratio of triblock copolymer to diblock copolymer is 3:2 to 1:3. In some aspects, the ratio of triblock copolymer to diblock copolymer is 3:2 to 1:2.5. In some aspects, the ratio of triblock copolymer to diblock copolymer is 3:2 to 1:2. In some aspects, the ratio of triblock copolymer to diblock copolymer is or 3:2 to 1:1.5. In some aspects, the ratio of triblock copolymer to diblock copolymer is 3:2 to 1:1.

In some embodiments, the psychiatric disease or disorder is schizophrenia, schizoaffective disorder, or bipolar disorder. In other embodiments, the psychiatric disease or disorder is schizophrenia or bipolar disorder. In other embodiments, the psychiatric disease or disorder is schizophrenia. In other embodiments, the psychiatric disease or disorder is schizoaffective disorder. In yet other embodiments, the psychiatric disease or disorder is bipolar disorder. In some aspects, the psychiatric disease is dementia. In some aspects, the psychiatric disease is bipolar disorder. In some aspects, the psychiatric disease is depression. In some aspects, the psychiatric disease is a manic disorder. In some aspects, the psychiatric disease is a psychotic episode. Method of treating as used herein refers to alleviating symptoms of the psychiatric disease or disorder. In some embodiments, method of treating includes a delay in time to relapse compared to a subject not receiving the pharmaceutical formulation. In some embodiments, method of treatment includes a reduced impending relapse rate as estimated using the Kaplan-Meier method. In some embodiments, method of treatment includes a reduced Observed Rate of Impending Relapse. In some embodiments, method of treatment includes Maintaining Stability including meeting all of the following criteria for at least 4 consecutive weeks: outpatient status; PANSS total score≤80; minimal presence of specific psychotic symptoms on the PANSS, as measured by a score of ≤4 on each of the following items: conceptual disorganization, suspiciousness, hallucinatory behavior, and unusual thought content; Clinical Global Impression of Severity (CGI-S) score≤4 (moderately ill); and Clinical Global Impression-Severity of Suicidality (CGI-SS) score≤2 (mildly suicidal) on Part 1 and ≤5 (minimally worsened) on Part 2. The percentage will be calculated as the number of patients who maintained stability at endpoint divided by the number of patients in the given treatment group. In some embodiments, method of treatment includes Achieving Remission. All remission criteria can be derived from PANSS items.

In some aspects, the present invention is directed to subcutaneous administration methods of treating a psychiatric disease or disorder in a subject. In particularly preferred embodiments, the subject is a human. In some embodiments, the subject is a human adult, aged greater than 18 years. In some embodiment, the subject is a human adolescent, aged 13 years to 18 years.

The methods of the invention comprise subcutaneous administration of a high concentration, low volume formulation of risperidone to a subject. In some embodiments, the subcutaneous administration is to the abdomen of the subject. In other embodiments, the subcutaneous administration is to the upper arm of the subject.

Subcutaneous administration of the risperidone formulation of the invention can result in in situ formation of solid or semi-solid implant. In these embodiments, the solid or semi-solid formulation is excisable (i.e., can be removed from the subject) following administration into the subject. A healthcare professional with skill in the art will be able to determine the preferred manner and time to excise.

In some aspects of the methods of the invention, the administration is with a frequency of no more than once every 21 days. In these aspects, the administration results in treating of the psychiatric disease or disorder for at least 21 days. In some embodiments, the administration is with a frequency of no more than once every 28 days. In these aspects, the administration results in treating of the psychiatric disease or disorder for at least 28 days. In some embodiments, the administration is with a frequency of no more than once every 30 days. In these aspects, the administration results in treating of the psychiatric disease or disorder for at least 30 days. In other embodiments, the administration is with a frequency of no more than once every 45 days. In these aspects, the administration results in treating of the psychiatric disease or disorder for at least 45 days. In other embodiments, the administration is with a frequency of no more than once every 56 days. In these aspects, the administration results in treating of the psychiatric disease or disorder for at least 56 days. In other embodiments, the administration is with a frequency of no more than once every 60 days. In these aspects, the administration results in treating of the psychiatric disease or disorder for at least 60 days.

According to the methods of the invention, the subject is administered 1 mL or less of a pharmaceutical formulation, as described herein. In some embodiments, the subject is administered 1 mL of the pharmaceutical formulation. In other embodiments, the subject is administered 0.9 mL or less of the pharmaceutical formulation. In other embodiments, the subject is administered 0.8 mL or less of the pharmaceutical formulation. In other embodiments, the subject is administered 0.7 mL or less of the pharmaceutical formulation.

In other embodiments, the subject is administered 0.6 mL or less of the pharmaceutical formulation. In other embodiments, the subject is administered 0.5 mL or less of the pharmaceutical formulation. In other embodiments, the subject is administered 0.4 mL or less of the pharmaceutical formulation. In other embodiments, the subject is administered 0.3 mL or less of the pharmaceutical formulation. In other embodiments, the subject is administered 0.2 mL or less of the pharmaceutical formulation. In other embodiments, the subject is administered 0.1 mL or less of the pharmaceutical formulation. In some embodiments, the subject is administered 0.1, 0.2, 0.3, 0.4, 0.5, 0.6, 0.7, 0.8, 0.9, or 1 mL of the pharmaceutical formulation. In some embodiments, the subject is administered 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, or 1 mL of the pharmaceutical formulation. In some embodiments, the pharmaceutical formulation comprises 250 mg/mL to 400 mg/mL of risperidone or a salt thereof, equivalent to risperidone.

According to the methods of the invention, the administered pharmaceutical formulations comprise risperidone, or a pharmaceutically acceptable salt thereof. In some embodiments, the pharmaceutical formulation comprises risperidone as risperidone base. In other embodiments, the pharmaceutical formulation comprises risperidone as a pharmaceutically acceptable salt of risperidone. In yet other embodiments, the pharmaceutical formulation comprises risperidone as a mixture of risperidone base and a pharmaceutically acceptable salt of risperidone.

The pharmaceutically effective amount of risperidone may vary depending on the extent of the subject's medical condition and the time required to deliver the risperidone. The methods of the invention are particularly directed to formulations having the risperidone (or salt thereof) at a concentration of at least 250 mg/mL, equivalent to risperidone, in a 1 mL or less delivery volume. While there is no critical upper limit on the amount of risperidone (or salt thereof), the formulation should be of a viscosity suitable for injection through a syringe needle such that it can effectively treat the psychiatric disease or disorder without exposing the subject to a risperidone overdose risk.

The concentration of risperidone, or a pharmaceutically acceptable salt thereof, used in the biodegradable drug delivery composition of the invention is at least 250 mg/mL equivalent to risperidone, preferably at least 300 mg/mL equivalent to risperidone. In some embodiments, the concentration of risperidone or a pharmaceutically acceptable salt thereof used in the biodegradable drug delivery composition of the invention is 250-300 mg/mL equivalent to risperidone. In other embodiments, the concentration of risperidone or a pharmaceutically acceptable salt thereof used in the biodegradable drug delivery composition of the invention is 300-400 mg/mL equivalent to risperidone. In other embodiments, the concentration of risperidone or a pharmaceutically acceptable salt thereof used in the biodegradable drug delivery composition of the invention is 300-350 mg/mL equivalent to risperidone. In other embodiments, the concentration of risperidone or a pharmaceutically acceptable salt thereof used in the biodegradable drug delivery composition of the invention is 350-400 mg/mL equivalent to risperidone.

Concentrations of risperidone, or the equivalent amount of a risperidone salt, in the formulations can range from about 250 mg/mL to 400 mg/mL, 260 mg/mL to 400 mg/mL, 270 mg/mL to 400 mg/mL, 280 mg/mL to 400 mg/mL, 290 mg/mL to 400 mg/mL, 300 mg/mL to 400 mg/mL, 310 mg/mL to 440 mg/mL, 315 mg/mL to 440 mg/mL, 320 mg/mL to 400 mg/mL, 330 mg/mL to 400 mg/mL, 340 mg/mL to 400 mg/mL, 350 mg/mL to 400 mg/mL, 360 mg/mL to 400 mg/mL, 370 mg/mL to 400 mg/mL, 380 mg/mL to 400 mg/mL, 390 mg/mL to 400 mg/mL, 260 mg/mL to 340 mg/mL, 270 mg/mL to 340 mg/mL, 280 mg/mL to 340 mg/mL In various embodiments, concentrations of risperidone, or the equivalent amount of a risperidone salt, in the formulations are (in mg/mL) 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, or 400.

In some aspects, the concentration of risperidone, or the equivalent amount of a risperidone salt, in the formulations is greater than 400 mg/mL, for example (in mg/mL), 410, 420, 430, 440, 450, 460, 470, 480, 490, or 500.

The length of the polyester chain is defined by its polyester to ethylene oxide molar ratio, which is between 0.5 to 3.5 or 0.5 to 2.5 or 0.5 to 22.3 for the triblock copolymer and 3 to 5 or 2 to 6 or 0.8 to 13 for the diblock copolymer. Thus, for example, if polylactic acid is used the chain length is defined by the lactic acid/ethylene oxide molar ratio.

The mass of the end-capped polyethylene glycol can range from 164 Da to 2,000 Da or from 100 Da to 2 kDa. It can range in the lower 100 to 300 Da range or in the 1 kDa to 2 kDa range.

The size of the polyethylene glycol chain ranges from 200 Da to 12 kDa in the biodegradable drug delivery composition or it can range from 400 Da to 12 kDa or 194 Da to 12 kDA.

The triblock copolymer is present in an amount of 3.0% to 45% (w/w %) of the total weight of the composition. In another aspect the triblock copolymer is present in an amount of 6% to 10% (w/w %) of the total weight of the composition. In yet another aspect the triblock copolymer is present in an amount of 20% to 40% (w/w %) of the total weight of the composition. In some embodiments, the triblock copolymer is present in an amount of 3% to 20% (w/w %) of the total weight of the formulation. In another aspect the triblock copolymer is present in an amount of 5% to 17% (w/w %) of the total weight of the formulation. In another aspect the triblock copolymer is present in an amount of 7% to 12% (w/w %) of the total weight of the formulation. In another aspect the triblock copolymer is present in an amount of 5% to 15% (w/w %) of the total weight of the formulation. In yet another aspect the triblock copolymer is present in an amount of about 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20% (w/w %) of the total weight of the formulation.

The diblock copolymer can be present in the biodegradable drug composition in an amount of 8% to 50% (w/w %) of the total weight of the composition. In another aspect the diblock copolymer is present in an amount of 10% to 20% (w/w %) of the total weight of the composition. In yet another aspect the diblock copolymer is present in an amount of 20% to 40% (w/w %) of the total weight of the composition. In some aspects, the diblock copolymer can be present in the biodegradable drug formulation in an amount of 6% to 30% (w/w %) of the total weight of the formulation. In another aspect the diblock copolymer is present in an amount of 8% to 30% (w/w %) of the total weight of the formulation. In some aspects of the methods of the invention, the diblock copolymer is present in an amount of about 8% to 25% (w/w %) of the total weight of the formulation. In another aspect the diblock copolymer is present in an amount of 10% to 25% (w/w %) of the total weight of the formulation. In some aspects of the methods of the invention, the diblock copolymer is present in an amount of about 10% to 20% (w/w %) of the total weight of the formulation. In yet another aspect the diblock copolymer is present in an amount of 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21%, 21.5%, 22%, 22.5%, 23%, 23.5%, 24%, 24.5%, 25%, 25.5%, 26%, 26.5%, 27%, 27.5%, 28%, 28.5%, 29%, 29.5%, 30% (w/w %) of the total weight of the formulation.

The polymers are present in the pharmaceutical formulations in an amount of 20% to 50% (w/w %) of the total weight of the composition. In another aspect the total weight of the polymers present in the biodegradable drug composition is 30% to 50% (w/w %) of the total weight of the composition. In yet another aspect the polymers are present in the biodegradable drug composition at 40% to 50% (w/w %) of the total weight of the composition.

In preferred aspects, the total amount of the triblock and diblock copolymers are present in an amount of 20% to 45% (w/w %) of the total weight of the formulation. In other preferred aspects, the total amount of the triblock and diblock copolymers present in the pharmaceutical formulations used herein is 20% to 30% (w/w %). In some embodiments of the methods of the invention, the triblock and diblock copolymers are present in a total amount of about 25% to about 45% (w/w %) of the total weight of the formulation. In yet another aspect the polymers are present in the biodegradable drug formulation at about 20%, 20.5%, 21%, 21.5%, 22%, 22.5%, 23%, 23.5%, 24%, 24.5%, 25%, 25.5%, 26%, 26.5%, 27%, 27.5%, 28%, 28.5%, 29%, 29.5%, 30%, 30.5%, 31%, 31.5%, 32%, 32.5%, 33%, 33.5%, 34%, 34.5%, 35%, 35.5%, 36%, 36.5%, 37%, 37.5%, 38%, 38.5%, 39%, 39.5%, 40%, 40.5%, 41%, 41.5%, 42%, 42.5%, 43%, 43.5%, 44%, 44.5%, or 45% (w/w %) of the total weight of the formulation.

The ratio of the biodegradable triblock copolymer (b) and the biodegradable diblock copolymer (c) is 1:3 to 1:8 or 1:1 to 1:19 or 3:2 to 1:19 in the pharmaceutical formulations of the invention.

In one embodiment, the ratio of the biodegradable triblock copolymer and the biodegradable diblock copolymer is selected from 3:2, 1:1, 1:2 1:3, 1:4, 1:5, 1:6, 1:7 and 1:8 or 1:1, 1:2, 1:3, 1:4, 1:5, 1:6, 1:7, 1:8, 1:9, 1:10, 1:11, 1:12, 1:13, 1:14, 1:15, 1:16, 1:17, 1:18 and 1:19.

In some embodiments, the ratio of the biodegradable triblock copolymer and the biodegradable diblock copolymer is 3:2. In other embodiments, the ratio of the biodegradable triblock copolymer and the biodegradable diblock copolymer is 1:4. In yet other embodiments, the ratio of the biodegradable triblock copolymer and the biodegradable CA diblock copolymer is 2:3.

The pharmaceutical formulations used in the methods of the disclosure can further comprise a pharmaceutically acceptable carrier, adjuvant or vehicle. An acceptable carrier can be saline, buffered saline and the like. The adjuvant can be formulated simultaneously when mixing the drug. In this regard the adjuvants that can be used are alum, aluminum phosphate, calcium phosphate, MPL™, CpG motifs, modified toxins, saponins, endogenous stimulatory adjuvants such as cytokines, Freunds complete and incomplete adjuvants, ISCOM type adjuvants, muramyl peptides and the like.

The pharmaceutical formulations used in the methods of the invention also include an organic solvent. In preferred embodiments, the organic solvent is a water-soluble organic solvent. The organic solvent that can be used in the methods described herein are selected from the group of: benzyl alcohol, benzyl benzoate, diethylene glycol dimethyl ether (Diglyme), diethylene glycol monoethyl ether (DEGMEE), dimethyl isosorbide (DMI), dimethyl sulfoxide (DMSO), ethyl acetate, ethyl benzoate, ethyl lactate, ethylene glycol monoethyl ether acetate, glycerol formal, methyl ethyl ketone, methyl isobutyl ketone, N-ethyl-2-pyrrolidone, N-methyl-2-pyrrolidinone (NMP), pyrrolidone-2, tetraglycol, triacetin, tributyrin, tripropionin (tripro), or triethylene glycol dimethyl ether (triglyme) and mixtures thereof. A preferred organic solvent is the water soluble organic solvent DMSO.

The organic solvent is present in an amount of 40% to 74% (w/w %) of the total composition. In another aspect the organic solvent used in the preparation of the biodegradable drug delivery composition is present in an amount of 50% to 60% (w/w %) of the total composition. In yet another aspect the solvent used in the preparation of the biodegradable drug delivery composition is present in an amount of 60% to 70% (w/w %) of the total composition. The organic solvent can be present in an amount of 15% to 45% or 40% to 74% (w/w %) of the total formulation. In another aspect the organic solvent used in the preparation of the pharmaceutical formulations is present in an amount of 40% to 50% (w/w %) of the total formulation.

In some embodiments, the organic solvent is DMSO. Triglycerides such as triacetin or tripropionin may also be included with the DMSO. The amount of DMSO that can be used in the pharmaceutical formulations of the methods of the present invention can be from 35% to 55% (w/w %), preferably from 35% to 45% (w/w %). In one aspect DMSO may include a triglyceride such as triacetin, tripropionin or mixtures thereof, in an amount of 10% to 15% (w/w %).

In the biodegradable drug delivery composition, also referenced herein as a pharmaceutical formulation, of the present invention, the amount of risperidone is released gradually over an extended period of time. This slow release can be continuous or discontinuous, linear or non-linear and can vary due to the composition of the triblock copolymer and diblock copolymer. Thus, the higher the lactic acid content of the triblock and diblock copolymers in comparison with the polyethylene glycol content, as well as the amount of triblock and diblock copolymers present in the biodegradable drug composition the longer the release of the active principle or drug. In other words, the higher the LA/EO molar ratio and the greater weight percentage of the triblock and diblock copolymers, the longer it will take for the active principle to be released from the drug composition. Volume may also affect release, with active principle released over a longer period of time from a larger volume than from a smaller volume [see data in example 2, below].

In one aspect, the biodegradable drug delivery composition can deliver the risperidone for at least 21 days. In one aspect, the biodegradable drug delivery composition can deliver the risperidone for 21 days up to about 90 days. In another aspect, the biodegradable drug delivery composition can deliver the risperidone for about 21 to 30 days or at about 28 to 31 days. In another aspect, the biodegradable drug delivery composition can deliver the risperidone for at least 30 days. In another aspect, the biodegradable drug delivery composition can deliver the risperidone for at about 56 to 63 days. In another aspect, the biodegradable drug delivery composition can deliver the risperidone for at least 60 days. In one aspect, the biodegradable drug delivery composition can deliver the risperidone for at least 90 days.

In the methods of the present invention, the administration results in an effective amount of risperidone being released from the formulation to treat the subject's psychiatric disease or disorder for an extended period of time. In some embodiments, the administration is effective in treating the subject's psychiatric disease or disorder for a duration of 21 days to 90 days. In some embodiments, the administration is effective in treating the subject's psychiatric disease or disorder for 28 days to 90 days. In other embodiments, the administration is effective in treating the subject's psychiatric disease or disorder for 28 or 30 days to 56 or 60 days. In some embodiments, the administration is effective in treating the subject's psychiatric disease or disorder for 28 days or for 30 days. In other embodiments, the administration is effective in treating the subject's psychiatric disease or disorder for 45 days. In other embodiments, the administration is effective in treating the subject's psychiatric disease or disorder for 56 days or for 60 days. In other embodiments, the administration is effective in treating the subject's psychiatric disease or disorder for 84 days or for 90 days. The dosing may be repeated after each period of, for example 28 or 56 days.

In most preferred aspects of the methods of the invention, the release of risperidone from the pharmaceutical formulation is such that therapeutically effective levels of risperidone are achieved within 24 hours of subcutaneous administration. With therapeutically effective levels of risperidone achieved within 24 hours of subcutaneous administration, alternative, immediate release risperidone formulations (for example, immediate release oral formulations or immediate release injectable formulations) are not required to ensure adequate risperidone levels in a subject. That is, a "loading dose" or supplemental oral dose of risperidone is not required in the methods of the invention. Thus, in some embodiments, the methods are implemented in the absence of a loading dose or supplemental oral risperidone.

Using the methods of the invention, a therapeutically effective amount of the risperidone will have been released by a target date. Thus, with an amount of a "30-day formulation," about 50 w %, or about 50 w % to about 80 w %, for example, 50, 55, 60, 65, 70, 75, or 80 w %, of the risperidone (or salt thereof) will have been cumulatively released by 30 days post administration, preferably with a near linear release profile. The term "cumulatively released" as used herein, refers to the total amount of risperidone (by weight) released by a particular point in time, as a percentage of the total amount of risperidone in the formulation. Cumulative release can be measured by, for example, the in vitro release (IVR) methods known in the art and described herein. Thus, with an amount of a "60-day formulation," about 75 w %, or about 75 w % to about 98 w %, for example, 75, 70, 85, 90, 91, 92, 93, 94, 95, 96, 97, or about 98 w %, of the risperidone (or salt thereof) will have been cumulatively released by 60 days post administration, preferably with a near linear release profile. Thus, the present invention provides a sustained, even release of risperidone over the desired time.

In some embodiments, less than about 15 w % of the risperidone in the formulation is cumulatively released at 24 hours post administration. In other embodiments, about 7 w % to about 15 w %, for example, 7, 8, 9, 10, 11, 12, 13, 14, or 15 w % of the risperidone in the formulation is cumulatively released at 24 hours post administration.

In some embodiments, about 50 w % to about 80 w %, for example, 50, 55, 60, 65, 70, 75, or 80 w % of the risperidone (or salt thereof) in the formulation is cumulatively released at 30 days post administration. In some embodiments, about 50 w % to about 80 w %, for example, 50, 55, 60, 65, 70, 75, or 80 w % of the risperidone (or salt thereof) in the formulation is cumulatively released at 28 days post administration.

In some embodiments, about 70 w % to about 98 w %, for example, 75, 70, 85, 90, 91, 92, 93, 94, 95, 96, 97, or about 98 w %, of the risperidone (or salt thereof) in the formulation is cumulatively released at 60 days post administration. In some embodiments, about 70 w % to about 98 w %, for example, 75, 70, 85, 90, 91, 92, 93, 94, 95, 96, 97, or about 98 w %, of the risperidone (or salt thereof) in the formulation is cumulatively released at 56 days post administration.

The pharmaceutical formulations used in the methods of the disclosure are injectable liquids at room temperature and can be injected through a syringe without excessive force. The compositions are also in situ forming and biodegradable and turn into solid or semi solid implants when injected into the animal.

In some aspects of the methods of the invention, the pharmaceutical formulation is administered from a pre-filled syringe (PFS). A PFS is a syringe which contains an appropriate amount of the pharmaceutical formulation and which is ready for subcutaneous administration, preferably by a healthcare professional. In some embodiments of the methods of the invention, the pharmaceutical formulation is administered from a single pre-filled syringe. In other embodiments, the pharmaceutical formulation is administered from more than one pre-filled syringe, for example, from 2, 3, 4, 5, or 6 or more pre-filled syringes.

According to the disclosure, the volume of the pharmaceutical formulation in the pre-filled syringe is 1 mL or less. In some embodiments, the volume of the pharmaceutical formulation in the pre-filled syringe is between 0.1 mL and 0.9 mL. In some embodiments, the volume of the pharmaceutical formulation in the pre-filled syringe is between 0.1 mL and 0.8 mL. In some embodiments, the volume of the pharmaceutical formulation in the pre-filled syringe is between 0.1 mL and 0.5 mL. In some embodiments, the volume of the pharmaceutical formulation in the pre-filled syringe is about 0.1 mL. In some embodiments, the volume of the pharmaceutical formulation in the pre-filled syringe is about 0.2 mL. In some embodiments, the volume of the pharmaceutical formulation in the pre-filled syringe is about 0.3 mL. In some embodiments, the volume of the pharmaceutical formulation in the pre-filled syringe is about 0.4 mL. In some embodiments, the volume of the pharmaceutical formulation in the pre-filled syringe is about 0.5 mL. In some embodiments, the volume of the pharmaceutical formulation in the pre-filled syringe is about 0.6 mL. In some embodiments, the volume of the pharmaceutical formulation in the pre-filled syringe is about 0.7 mL. In some embodiments, the volume of the pharmaceutical formulation in the pre-filled syringe is about 0.8 mL. In some embodiments, the volume of the pharmaceutical formulation in the pre-filled syringe is about 0.9 mL. In some embodiments, the volume of the pharmaceutical formulation in the pre-filled syringe is about 1.0 mL. In some embodiments, the amount of risperidone in pharmaceutical formulation is 50 mg in a volume of about 0.14 mL. In some embodiments, the amount of risperidone in pharmaceutical formulation is 100 mg in a volume of about 0.28 mL. In some embodiments, the amount of risperidone in pharmaceutical formulation is 150 mg in a volume of about 0.42 mL. In some embodiments, the amount of risperidone in pharmaceutical formulation is 200 mg in a volume of about 0.56 mL. In some embodiments, the amount of risperidone in pharmaceutical formulation is 250 mg in a volume of about 0.7 mL. In some embodiments, the amount of risperidone in pharmaceutical formulation is 300 mg in a volume of about 0.84 mL.

Many psychiatric disorders are chronic conditions that require continuous treatment to moderate symptoms and prevent relapse. Thus, the methods of the present invention are capable of being implemented over extended periods of time. In some embodiments, the methods are implemented over a period of at least 6 months. In other embodiments, the methods are implemented over a period of at least 12 months. In other embodiments, the methods are implemented over a period of at least 15 months. In other embodiments, the methods are implemented over a period of at least 24 months.

Further provided is a pharmaceutical formulation comprising 1 mL or less of:

a) risperidone, or a pharmaceutically acceptable salt thereof, at a concentration of about 250-400 mg/mL, equivalent to risperidone;

b) a biodegradable triblock copolymer having the formula:

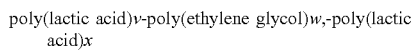

poly(lactic acid)$v$-poly(ethylene glycol)$w$,-poly(lactic acid)$x$ wherein v and x are the number of repeat units ranging from 24 to 682 and w is the number of repeat units ranging from 4 to 273 and v=x or v≠x;

c) a biodegradable diblock copolymer having the formula:

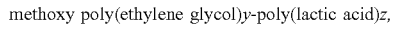

methoxy poly(ethylene glycol)$y$-poly(lactic acid)$z$, wherein y and z are the number of repeat units, wherein y is the number of repeat units ranging from 3 to 45 and z is the number of units ranging from 7 to 327; and wherein the ratio of the biodegradable triblock copolymer of (b) and the biodegradable diblock copolymer of (c) is 1:3 to 1:8 or 1:1 to 1:19 or 3:2 to 1:19, in said formulation, which is insoluble in an aqueous environment, for use in treating a psychiatric disease or disorder.

Methods for preparing the pharmaceutical formulations used in the methods of the invention are disclosed in, for example U.S. Pat. No. 9,023,897, incorporated by reference herein.

Some mPEG-OH are contaminated with a small amount of OH-PEG-OH. By following the methods of the present invention and using contaminated mPEG-OH the final product would be mPEG-PLA contaminated with a small amount of PLA-PEG-PLA, which is encompassed by the present invention.

For the foregoing embodiments, each embodiment disclosed herein is contemplated as being applicable to each of the other disclosed embodiments. For instance, the elements recited in the method embodiments can be used in the pharmaceutical composition or formulation embodiments described herein and vice versa.

The following examples are for illustrative purposes, and are intended to be nonlimiting. Those of skill in the art will readily recognize a variety of features which can be changed or modified to yield essentially the same results.

EXAMPLES

Example 1. In Vitro Release (IVR) Model

The in vitro model set-up was based on the USP II dissolutest technique, where the in vitro release of the drug formulations are followed up in tubes containing an aqueous buffer maintained at +37° C. under constant agitation. Approximately 100 or 170 mg of the formulations were injected using a 0.5-mL syringe mounted with a 23 G needle inside a Falcon® tube prefilled with 50 mL of Krebs-Ringer-Tris buffer (KRT, pH 7.4), and immediately incubated at +37° C. under constant orbital agitation rate (180 rpm). The depots freely formed instantly upon contact with the buffer due to the insolubility of the copolymers in water, which is intended to mimic the implant formation in the subcutaneous tissue in vivo.

The in vitro release for each formulation was performed in duplicate. At predetermined time-points, the release buffer was sampled and refreshed. Special care was given to avoid losing depot fragments (when present) during buffer replacement. When an IVR was stopped, the amount of active agent in the remaining depot was determined by HPLC to assess the mass balance and ascertain that the remaining amount of active agent in the depot correlated with the cumulative release. Briefly, the remaining depot was solubilized in 10 mL of acetonitrile. The solution was mixed using a vortex mixer until complete dissolution and then, 10 mL of ultrapure water were added. The mixture was shaken once again prior to HPLC analysis.

Preparation of Stock Solutions, Standard and Quality Control Samples

A stock solution was prepared by dissolving risperidone in acetonitrile/H$_2$O mixture (50/50 v/v) in order to achieve a 200 µg/mL solution of risperidone. This "mother solution" was stored at +2-8° C. and showed stability over a minimum of 5 months. Starting from this mother solution, calibration standards were prepared by dilution in the same sample solvent mixture as above. Six dilutions were performed to obtain calibration standards of 1, 5, 10, 25, 50, 100 and 200 µg/mL.

Additional working solutions containing 0.10, 0.25, 0.50 and 0.75 µg/mL were prepared likewise by further diluting the standard 10 µg/mL. These further diluted samples were specifically used to investigate the limit of detection (LOD) and the limit of quantification (LOQ) of the chromatographic method.

A series of three accuracy standards (10, 100 and 200 µg/mL) were also independently prepared by dilution of the starting mother solution (200 µg/mL) using the same sample solvent as described above. These standards were used to assess the level of accuracy of the developed method.

Instruments and Chromatographic Conditions

HPLC equipment of a Waters 269S Separation Module equipped with a Waters 2487 Dual wavelength UV detector set at 280 nm (corresponding to the maximum absorption wavelength of risperidone) was used. The separation column (150 mm×4.6 mm) was packed with Kinetex C18 of 5-µm particle size. The following Table 1 summarizes the mobile phase gradient used in this study. A flow rate of 1 mL/min was used, and the column temperature was set to +30° C. The injection volume of the sample was 10 µL.

TABLE 1

| Time (min) | Acetonitrile (%) | H$_2$O/CH$_3$COONH$_4$ (%) |
|---|---|---|
| 0 | 25 | 75 |
| 7 | 70 | 30 |
| 7.5 | 95 | 5 |
| 9 | 25 | 75 |
| 12 | 25 | 75 |

According to the above conditions, the retention time of risperidone is 5.5 min. Linearity was assessed throughout the analysis of the standards (1, 5, 10, 25, 50, 100 and 200 µg/mL). Calibration was set based on each standard peak area. The curve of best fit was determined using linear regression analysis and gave a r$^2$>0.9999. The accuracy was determined by calculating the relative standard deviation (RSD) between the mean assayed concentration of three accuracy standards, namely 10, 100 and 200 µg/mL. The RSD was <0.1% for all accuracy standards, and the recovery ranged between 99.7 to 101.9% of the target concentration. The LOD was calculated to be 0.1 µg/mL (corresponding to three times the average baseline noise). The LOQ was assessed as the lowest concentration that allowed a 90% recovery of the target drug concentration. LOQ was found to be 0.5 µg/mL.

Injectability was measured according to a standard zed operating procedure (SOP, Texturometer Use (LA-PR-EQ-6-1-EN)). The method was inspired from the previous work of F. Cilurzo et al. The apparatus used for injectability measurements was a Friction Tester FTPlus (Lloyd Instruments) connected with the Nexygen Plus software. Briefly, the injectability test was carried out by fixing the crosshead speed to 1.1 mL/min, using a 1-mL CODAN syringe mounted with a 23 G or 25 G needle. The syringe was prefilled with at least 0.5 mL of the formulation to be tested. The Dynamic Glide Force (DGF) (i.e. the average force in Newton (N) required to sustain the movement of the plunger to expel the formulation out of the syringe) was then measured in each study. F. Cilurzo et al demonstrated "this parameter is representative of a manual syringe delivery to patient." (Cilurzo, F, et al., Injectability Evaluation: An Open Issue. AAPS PharmSciTech. 2011 2: 604-609).

Example 2. Risperidone Formulations

A formulation of risperidone with an amount of risperidone of at least 250 mg/mL, for example, at least 300 mg/mL and up to about 400 mg/mL for an injection volume of ≤1 mL.

Preparation of Risperidone Particles

Particles of risperidone may be prepared using supermicronization, micronization or milled sourcing.

Dose Adjustment by Volume Injection

A 2-fold increase in injection volume resulted in a non-proportional increase in the release kinetics as evidenced by a shift of the 75% cumulative release between 125 mg and 250 mg depot. A depot of 250 mg would release its risperidone cargo over a longer period of time than would a 125 mg depot.

Exemplary formulations are shown in Table 2. Given percentages are weight percentages from total formulation composition.

TABLE 2

| Formulations: | RSP mg/mL | TB (PaRb)* | % TB | DB (dPaRb)* | % DB | % total polymer | Ratio TB:DB | % DMSO |
|---|---|---|---|---|---|---|---|---|
| F1L | 120 | P1R4 | 24 | dP0.35R5.5 | 16 | 40 | 3:2 | 50 |
| F2L | 180 | P1R4 | 24 | dP0.35R5.5 | 16 | 40 | 3:2 | 45 |
| F3L | 240 | P1R4 | 24 | dP0.35R5.5 | 16 | 40 | 3:2 | 40 |
| F3 | 300 | P2R3.5 | 8 | dP2R3 | 12 | 20 | 2:3 | 55 |
| F8 | 360 | P2R3.5 | 8 | dP0.35R5.5 | 12 | 20 | 2:3 | 50 |
| F11 | 360 | P1R4 | 18 | dP0.35R5.5 | 12 | 30 | 3:2 | 40 |
| F15 | 360 | P1R4 | 10 | dP0.35R5.5 | 15 | 25 | 2:3 | 45 |
| F24 | 360 | P1R6 | 10 | dP0.35R5.5 | 15 | 25 | 2:3 | 45 |
| F25 | 360 | P1R6 | 10 | dP0.35R8 | 15 | 25 | 2:3 | 45 |
| F28 | 480 | P1R4 | 8 | dP0.35R5.5 | 12 | 20 | 2:3 | 40 |
| F29 | 360 | P1R6 | 20 | dP2R3 | 5 | 25 | 4:1 | 45 |
| F30 | 360 | P1R6 | 17.5 | dP2R3 | 7.5 | 25 | 2.5:1 | 45 |
| F32 | 360 | P1R6 | 10 | dP1R3.5 | 15 | 25 | 2:3 | 45 |
| F33 | 360 | P1R6 | 10 | dP1R5 | 15 | 25 | 2:3 | 45 |
| F34 | 360 | P1R6 | 7.5 | dP1R5 | 17.5 | 25 | 1:2.5 | 45 |
| F36 | 360 | P1R6 | 15 | dP0.35R8 | 10 | 25 | 3:2 | 45 |
| F37 | 360 | P1R6 | 10 | dP2R3.5 | 15 | 25 | 2:3 | 45 |
| F39 | 360 | P1R6 | 11 | dP2R3 | 16.5 | 27.5 | 2:3 | 42.5 |
| F78 | 360 | P1R6 | 10 | dP2R3 | 15 | 25 | 2:3 | 45 |
| F79 | 341 | P1R6 | 17.07 | dP2R3 | 11.38 | 28.45 | 3:2 | 43.1 |
| F80 | 429 | P1R6 | 15.32 | dP2R3 | 10.22 | 25.54 | 2:2 | 38.71 |
| F81 | 288 | P1R6 | 4.79 | dP2R3 | 19.17 | 23.96 | 1:4 | 52.08 |
| F82 | 341 | P1R6 | 5.59 | dP2R3 | 22.76 | 28.45 | 1:4 | 43.1 |
| F83 | 367 | P1R6 | 13.12 | dP2R3 | 8.74 | 21.86 | 3:2 | 47.53 |
| F84 | 429 | P1R6 | 5.11 | dP2R3 | 20.43 | 25.54 | 1:4 | 38.7 |
| F85 | 401 | P1R6 | 4.79 | dP2R3 | 19.11 | 23.89 | 1:4 | 42.66 |
| F86 | 288 | P1R6 | 14.38 | dP2R3 | 9.58 | 23.96 | 3:2 | 52.08 |
| F89 | 360 | P1R6 | 5 | dP2R3 | 22.5 | 27.5 | 1:4.5 | 42.5 |
| F90 | 360 | P1R6 | 10 | dP2R3 | 17.5 | 27.5 | 1:1.75 | 42.5 |
| F93 | 360 | P1R6 | 5.5 | dP2R3 | 24.5 | 30 | 1:4.5 | 40 |

*PaRb represents a TB copolymer where a is the size of the PEG chain in kDa and b is the lactic acid/ethylene oxide (LA/EO) molar ratio Cumulative release of the formulations shown in Table 2 is provided in Tables 3 and 4.

"Mean" refers to % of total release.

TABLE 3

| Time (days) | F81 Mean | F81 SD | F82 Mean | F82 SD | F83 Mean | F83 SD | F84 Mean | F84 SD | F85 Mean | F85 SD | F86 Mean | F86 SD |
|---|---|---|---|---|---|---|---|---|---|---|---|---|
| 0.08 | 1.6 | 0.1 | 1.5 | 0.1 | 1.7 | 0.1 | 1.1 | 0.1 | 1.3 | 0.1 | 1.7 | 0.1 |
| 0.17 | 2.8 | 0.2 | 2.2 | 0.1 | 2.9 | 0.2 | 1.9 | 0.1 | 2.4 | 0.1 | 2.7 | 0.1 |
| 0.25 | 4.2 | 0.3 | 3.2 | 0.2 | 4.2 | 0.2 | 2.8 | 0.1 | 3.4 | 0.2 | 3.8 | 0.1 |
| 1 | 12.5 | 0.3 | 9.8 | 0.2 | 12.4 | 0.5 | 10.8 | 0.1 | 10.9 | 0.2 | 13.7 | 0.3 |
| 2 | 17.6 | 0.5 | 16.2 | 0.4 | 17.9 | 0.3 | 16.5 | 0.3 | 16 | 0.6 | 20.6 | 0.3 |
| 3 | 20.8 | 0.7 | 22.1 | 0.3 | 22.2 | 0.1 | 20.6 | 0.4 | 19.4 | 0.4 | 24.6 | 0.4 |
| 6 | 27.6 | 1 | 32.5 | 0.2 | 31.3 | 0.7 | 28.5 | 0.5 | 26.3 | 0.6 | 33 | 0.6 |
| 10 | 34.2 | 1 | 41.3 | 0.2 | 40.6 | 1.4 | 36.1 | 0.4 | 33.2 | 0.8 | 41.1 | 0.7 |
| 14 | 39.5 | 0.8 | 47.2 | 0.1 | | | 41.3 | 0.5 | 38.5 | 1 | 47.1 | 0.7 |
| 17 | 43.5 | 1 | 51 | 0.2 | 51.9 | 0.9 | 45.1 | 0.6 | 42.5 | 1.1 | 51.5 | 0.5 |
| 21 | 47.3 | 0.9 | 54.3 | 0.2 | 56.2 | 0.9 | 48.3 | 0.7 | 46.1 | 1.2 | 55.4 | 0.4 |
| 24 | 52.2 | 1 | 58.5 | 0.3 | 62 | 1.1 | 52.8 | 0.6 | 51 | 1.3 | 60.5 | 0.6 |
| 28 | 56.5 | 1.2 | 61.8 | 0.3 | 66.5 | 1.2 | 56.2 | 0.6 | 55 | 1.3 | 64.9 | 0.6 |
| 31 | 59.9 | 1.2 | 65 | 0.3 | 70.3 | 1.2 | 60.1 | 0.6 | 58.2 | 1.2 | 68.8 | 0.6 |
| 34 | 64.7 | 1.2 | 68.4 | 0.4 | 74.9 | 1.2 | 63.8 | 0.6 | 62.7 | 1.2 | 73.2 | 0.6 |
| 42 | 73 | 1.2 | 74 | 0.4 | 81.8 | 1.2 | 70.1 | 0.6 | 70.1 | 1.2 | 80 | 0.6 |
| 49 | 79.5 | 0.9 | 78.6 | 0.5 | 87.2 | 1.1 | 75.3 | 0.6 | 75.9 | 1.1 | 85.4 | 0.5 |
| 56 | 85.4 | 0.9 | 83.1 | 0.4 | 92.1 | 1.1 | 80.3 | 0.6 | 81.5 | 0.9 | 90.8 | 0.3 |
| 63 | 89.7 | 0.9 | 86.5 | 0.4 | 95.6 | 0.3 | 84.1 | 0.7 | 85.3 | 0.9 | 94.5 | 0.2 |
| 70 | 93.4 | 0.8 | 89.5 | 0.4 | 98.1 | 0.3 | 87.3 | 0.6 | 88.8 | 0.8 | 97.5 | 0.2 |
| 77 | 96.1 | 0.6 | 92 | 0.4 | | | 89.9 | 0.6 | 91.3 | 0.7 | | |
| 84 | | | 94.1 | 0.7 | | | 92.8 | 0.5 | 93.8 | 0.6 | | |
| 91 | | | 95.9 | 0.7 | | | 94.7 | 0.5 | 95.6 | 0.5 | | |
| 105 | | | 98.9 | 0.8 | | | 97.7 | 0.6 | 98 | 0.3 | | |
| 119 | | | | | | | 99.6 | 0.6 | | | | |

TABLE 4

| Time (days) | F89 Mean | F89 SD | F90 Mean | F90 SD | F93 Mean | F93 SD |
|---|---|---|---|---|---|---|
| 0.08 | 1.4 | 0 | 1.3 | 0 | 1.3 | 0 |
| 0.17 | 2.1 | 0.1 | 2 | 0 | 2.4 | 0.1 |
| 0.25 | 3 | 0.1 | 2.9 | 0.1 | 3.3 | 0.2 |
| 1 | 9 | 0.5 | 8.9 | 0.2 | 8.9 | 0.2 |
| 2 | 15.1 | 1 | 15.1 | 0.6 | 14.8 | 0.1 |
| 3 | 20.3 | 0.9 | 20.8 | 0.8 | 20.5 | 0.2 |
| 6 | 30.3 | 0.9 | 32.2 | 0.5 | 32 | 0.6 |
| 10 | 38.6 | 1 | 41.4 | 0.5 | 40.5 | 0.6 |
| 14 | 44 | 1.1 | 47.6 | 0.6 | 46.9 | 0.4 |
| 17 | 47.4 | 1.1 | 51.4 | 0.6 | 50.6 | 0.4 |
| 21 | 52.2 | 1.1 | 55.8 | 0.5 | 54.9 | 0.3 |
| 24 | 55.3 | 0.9 | 58.9 | 0.5 | 57.9 | 0.4 |
| 28 | 59.2 | 1.1 | 62.4 | 1 | 61.1 | 0.4 |
| 31 | 61.6 | 1.1 | 64.8 | 1 | 63.3 | 0.4 |
| 34 | 64.6 | 1.2 | 67.8 | 0.9 | 66.4 | 0.5 |
| 42 | 69.1 | 1.1 | 72.1 | 0.8 | 71 | 0.5 |
| 49 | 72.7 | 1 | 75.7 | 0.8 | 74.7 | 0.6 |
| 56 | 76.3 | 1 | 79.4 | 0.7 | 78.6 | 0.8 |
| 63 | 79.2 | 0.9 | 82.3 | 0.6 | 81.5 | 0.8 |
| 70 | 82.2 | 0.9 | 85.4 | 0.5 | 84.7 | 0.7 |
| 77 | 84.7 | 0.9 | 88.1 | 0.4 | 89 | 2.9 |
| 84 | 87.1 | 0.7 | 91 | 0.2 | 92.5 | 4.7 |
| 91 | 89.3 | 0.7 | 92.8 | 0 | 94.7 | 5.3 |
| 105 | 92.2 | 0.7 | 95.5 | 0.2 | 95.8 | 5.9 |
| 119 | 93.8 | 0.7 | 96.9 | 0.1 | 96.8 | 5.8 |
| | 94.4 | 0.6 | | | 97.3 | 5.8 |

Example 3 Excision Study

The possibility to excise the compositions from the subcutaneous (sc) space was tested. Without wishing to be bound to any particular theory, a health care professional may consider post-administration implant excision in case of adverse events.

Compositions were subcutaneously injected into the interscapular and flank area of rats, dogs, mini-swine and pigs.

In one study, the feasibility of locating and excising the sc injected implant for long-acting release of risperidone by clinically relevant imaging techniques ultrasound and MRI in mini-swine. Two *Sus scrofa* Yucatan mini-swine were injected sc with 50 and 150 mg risperidone formulation, corresponding to 140- and 420-μL volumes, respectively, in the flank of the animal. In addition, the animals were injected sc with 3 vehicle formulations (non-API control formulation) having a volume range of 70 to 840 μL for a total of 5 implants per animal (2 risperidone, 3 vehicle)

MRI (Magnetom Sonata Syngo 1.5 T; Siemens), ultrasound (FujiFilm Vevo MD apparatus for 15, 30, and 50 MHz frequencies), and Siemens Acuson SC2000 apparel (for 9 MHz frequency) imaging modalities were used to locate the implants at 4 hours post-injection and on days 1, 3, 6, 14, 20, 27, and 35. Excision of an implant was performed on day 14 post-injection, and PK samples were collected prior and up to 72 hours after, to validate complete removal.

MRI was a useful visual support for the depth and size of the implant throughout the study. Ultrasound imaging at 4 hours post-dosing was challenging and the implants with volumes of 70 to 140 μL were difficult to locate. On days 1 to 6, the echogenicity of the depot was variable but viewable using lower frequencies (9 and 15 MHz). On days 14 to 35, ultrasound images using both 9- and 15 MHz probes were clear, aiding in locating the small-injected volumes. Higher frequency (30 and 50 MHz) probes did not assist in locating the implant. A risperidone implant was excised surgically on day 14 post-injection, after imaging and palpation at the location of the site of injection. No trace of the implant could be imaged, and plasma levels of risperidone dropped immediately post-excision. The excision site healed within a few days post-surgery, and the animals' recovery, monitored for up to 2 weeks post-excision, was good. Overall, locating the sc implant by clinically relevant imaging techniques such as ultrasound using 9 and 15 MHz probes, and MRI was proven to be feasible. Excision was successful and thorough, allowing removal of risperidone from systemic circulation, if needed.

Example 4 Pharmacokinetic Study

A two-part clinical study was conducted to (part 1) evaluate the safety, tolerability and pharmacokinetics of the risperidone prolonged-release suspensions disclosed herein for subcutaneous injection and (part 2) evaluate the influence of manipulation of the injection site and the site of administration on the pharmacokinetics of the risperidone.

This study was performed on 53 healthy volunteers and 6 other patients who received an injection of the formulation vehicle without risperidone.

Part 1 of this study was an open-label, nonrandomized, ascending dose study (5 cohorts), and Part 2 of this study was an open-label, nonrandomized, ascending dose study (2 cohorts).

Example 5 SAD/MAD Study

A sequential, single ascending dose and multiple ascending dose study was conducted to evaluate the safety, tolerability, and pharmacokinetics of the risperidone extended-release injectable suspension disclosed herein for subcutaneous use, in patients with schizophrenia or schizoaffective disorder.

- No serious adverse reactions linked to the formulations disclosed herein
- The treatment methods demonstrated a favorable risk/benefit profile
- No significant change in pharmacokinetic parameters were observed during change of the injection area
- Validation of doses and target durations: 1-month (Q1M) and 2-month (Q2M) products The results from the trials in Examples 4 and 5 have shown that the formulations disclosed herein with 1-month and 2-month release profiles in various doses provide a rapid establishment of clinically-relevant risperidone plasma concentrations which peak during the first 24 hours, avoiding any need for oral complementation after treatment initiation, and then slowly decrease over one to two months, respectively. Doses were selected based on the comparability of plasma concentrations with those obtained with oral risperidone over a 24-hour dosing interval, with the aim to ensure adequate exposure throughout the dosing period.

Safety, including local tolerance at the site of injection, was studied in the two clinical trials of Examples 4 and 5. The results from the two trials, for a total of 147 individuals, showed a safety profile consistent with the known safety profile of risperidone, along with good local tolerability at the site of injection. Two serious adverse events have been reported from cohort 8 of the study of Example 5, both events were assessed by both the investigator and sponsor as not related to the risperidone formulation. There were no other serious adverse events in patients who received the risperidone formulation in this study.

The safety analysis for the study of Example 5 is shown in Table 5.

TABLE 5

| | Cohort 1 (50 mg) 1 dose, Abd (N = 12) | Cohort 2 (75 mg) 1 dose, Abd (N = 12) | Cohort 3 (100 mg) 1 dose, Abd (N = 12) | Cohort 4 (150 mg) 1 dose, Abd (N = 12) | Cohort 5 (225 mg) 1 dose, Abd (N = 12) | Cohort 6 (50 mg) 3 doses, Abd (N = 12) | Cohort 7 (75 mg) 3 doses, Abd (N = 12) | Cohort 8 (225 mg) 1 dose, Upper arm (N = 15) |
|---|---|---|---|---|---|---|---|---|
| Analysis of adverse effects observed during the clinical phase | | | | | | | | |
| Frequency of appearance of treatment-related adverse reactions | 3 patients (25%) | 4 patients (33%) | 5 patients (42%) | 3 patients (25%) | 11 patients (92%) | 3 patients (25%) | 5 patients (42%) | 12 patients (80%) |
| Most commonly observed treatment-related adverse reactions | Weight increase, injection site pain, erythema, swelling, pruritus and induration, blood creatinine phosphokinase increase, headache and sedation. | | | | | | | |
| Characteristics of treatment-related adverse reactions | Mild to moderate All injection site adverse events were transient and resolved. None were serious | | | | | | | |
| Results of laboratory tests, vital signs, ECG and psychiatric assessment scales | Consistent with known safety profile of risperidone and did not reveal any new safety signals for risperidone LAI | | | | | | | |

Abd = abdomen sc injection

The study population was 99 schizophrenic patients, with 88 patients included in the safety component of the study.

The study design was an open-label, single ascending dose (SAD) and multiple ascending dose (MAD) study (8 cohorts).

The studies of Examples 3 and 4 together demonstrated several points:

The safety profile of the formulations disclosed herein was consistent with the other risperidone formulations;

Example 6: Phase 3 Clinical Trial with Risperidone Formulation

Aim of the Study: The purpose of the study is to evaluate the efficacy, safety, and tolerability of different dose regimens of the Risperidone Formulation described herein administered subcutaneously as compared to placebo during maintenance treatment in adult and adolescent patients with schizophrenia.

Study Design: Double-blind, randomized, relapse prevention study comparing two Risperidone formulations of the disclosure at a therapeutic dose with placebo SC (once month, Q1M) in a 1:1:1 ratio.

Study Population: Male and female patients, 13 to 65 years of age, who have a confirmed diagnosis of schizophrenia, are clinically stable, and are eligible for risperidone treatment.

Study Drug: 250-400 mg/mL risperidone in formulations as disclosed herein. The study drug is presented in glass vial which includes an amount of risperidone formulation or a pre-filled syringe (PFS) including an amount of the risperidone formulation. The study drug is tested for comparability of risperidone exposure upon subcutaneous administration once every 28-30 days (Q1M) or once every 56-60 days (Q2M) and oral risperidone tablets.

Primary and Secondary Outcome Measures:
Primary Outcome Measure:
 1. Time to Impending Relapse [Time Frame: 15 months]
Is calculated as the earliest date the patient meets ≥1 of the impending relapse criteria
Secondary Outcome Measures:
 1. Time to impending relapse [Time Frame: 15 months]
As defined under the primary objective in the total population (adults and adolescents).
 2. Time to impending relapse in adolescent patients with schizophrenia
 3. Impending Relapse Rate [Time Frame: Week 24]
This rate will be estimated using the Kaplan-Meier method.
 4. Observed Rate of Impending Relapse [Time Frame: 15 months]
Calculated as the number of patients who relapsed by endpoint divided by the number of patients in each treatment group.
 5. Percentage of Patients Who Maintain Stability [Time Frame: 15 months]
Stability is defined as meeting all of the following criteria for at least 4 consecutive weeks: outpatient status; PANSS total score≤80; minimal presence of specific psychotic symptoms on the PANSS, as measured by a score of ≤4 on each of the following items: conceptual disorganization, suspiciousness, hallucinatory behavior, and unusual thought content; Clinical Global Impression of Severity (CGI-S) score≤4 (moderately ill); and Clinical Global Impression-Severity of Suicidality (CGI-SS) score≤2 (mildly suicidal) on Part 1 and ≤5 (minimally worsened) on Part 2. The percentage will be calculated as the number of patients who maintained stability at endpoint divided by the number of patients in the given treatment group.
 6. Percentage of Patients Achieving Remission [Time Frame: 15 months]
Positive symptom, negative symptom, and overall symptom remission will be examined and are defined by Andreasen et al (2005), including severity and duration criteria. All remission criteria can be derived from PANSS items.
 7. Percentage of Participants with Adverse Events [Time Frame: 15 months]

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied without departing from the spirit and scope of the invention.

All patents, patent applications, and publications disclosed herein are herein incorporated by reference to the same extent as if each individual publication was specifically and individually indicated to be incorporated by reference. It should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention claimed is:

1. A method of treating a psychiatric disease or disorder in a subject, comprising subcutaneously administering to the subject with a frequency of no more than once every 21 days:
  1 mL or less of a pharmaceutical formulation comprising:
  a) risperidone, or a pharmaceutically acceptable salt thereof, at a concentration of about 250-400 mg/mL, equivalent to risperidone;
  b) a biodegradable triblock copolymer having the formula:

$$\text{poly(lactic acid)}_v\text{-poly(ethylene glycol)}_w\text{-poly(lactic acid)}_x$$

wherein v and x are the number of repeat units ranging from 24 to 682 and w is the number of repeat units ranging from 4 to 273 and v=x or v≠x;
  c) a biodegradable diblock copolymer having the formula:

$$\text{methoxy poly(ethylene glycol)}_y\text{-poly(lactic acid)}_z,$$

wherein y and z are the number of repeat units, wherein y is the number of repeat units ranging from 3 to 45 and z is the number of units ranging from 7 to 327; and
  wherein the ratio of the biodegradable triblock copolymer of (b) and the biodegradable diblock copolymer of (c) is 1:3 to 1:8 or 1:1 to 1:19 or 3:2 to 1:19, in said formulation, which is insoluble in an aqueous environment.

2. The method of claim 1, wherein the risperidone is risperidone base.

3. The method of claim 1, wherein the concentration of the risperidone or the pharmaceutically acceptable salt thereof, is 300 mg/mL to 400 mg/mL, equivalent to risperidone.

4. The method of claim 1, wherein the triblock copolymer is present in an amount of about 3% to 20% (w/w %) of the total weight of the formulation.

5. The method of claim 4, wherein the triblock copolymer is present in an amount of about 5% to 15% (w/w %) of the total weight of the formulation.

6. The method of claim 1, wherein the diblock copolymer is present in an amount of about 8% to 25% (w/w %) of the total weight of the formulation.

7. The method of claim 6, wherein the diblock copolymer is present in an amount of about 10% to 20% (w/w %) of the total weight of the formulation.

8. The method of claim 1, wherein the triblock and diblock copolymers are present in a total amount of about 20% to about 50% (w/w %) of the total weight of the formulation.

9. The method of claim 8, wherein the triblock and diblock copolymers are present in a total amount of about 20% to 30% (w/w %) of the total weight of the formulation.

10. The method of claim 1, wherein the formulation further comprises a water soluble organic solvent that is DMSO.

11. The method of claim 10, wherein the formulation further comprises triacetin, tripropionin, or a mixture thereof.

12. The method of claim 10, wherein the organic solvent is present in an amount of about 35% to about 55% (w/w %) of the total weight of the formulation.

13. The method of claim 1, wherein the administration is effective in treating the subject's psychiatric disease or disorder for 21 days to 90 days.

14. The method of claim 1, wherein the administration is effective in treating the subject's psychiatric disease or disorder for 28 days to 90 days.

15. The method of claim 1, wherein the administration is effective in treating the subject's psychiatric disease or disorder for 28 days to 56 days.

16. The method of claim 1, wherein less than about 15 w % of the risperidone in the formulation is cumulatively released at 24 hours post administration.

17. The method of claim 16, wherein about 7 w % to about 15 w % of the risperidone in the formulation is cumulatively released at 24 hours post administration.

18. The method of claim 13, wherein about 50 w % to about 80 w % of the risperidone in the formulation is cumulatively released at 30 days post administration.

19. The method of claim 13, wherein about 70 w % to about 98% w % of the risperidone in the formulation is cumulatively released at 60 days administration.

20. The method of claim 13, wherein the cumulative release is determined by in vitro release (IVR) method disclosed herein.

21. The method of claim 1, wherein the psychiatric disease or disorder is schizophrenia or bipolar disorder.

22. The method of claim 1, wherein the method is implemented in the absence of a loading dose or supplemental oral risperidone.

23. The method of claim 1 which comprises treating the subject over a period of at least 6 months.

24. The method of claim 23, which comprises treating the subject over a period of at least 15 months.

25. The method of claim 1, wherein the formulation is presented in a single prefilled syringe (PFS).

26. The method of claim 25, wherein the volume in the prefilled syringe is between 0.1 mL and 0.8 mL.

27. The method of claim 1, wherein the administration is subcutaneous into the abdomen.

28. The method of claim 1, wherein the administration is subcutaneous into the upper arm.

29. The method of claim 1, wherein the formulation is excisable following administration into the subject.

30. A pharmaceutical formulation comprising 1 mL or less of:
a) risperidone, or a pharmaceutically acceptable salt thereof, at a concentration of about 250-400 mg/mL, equivalent to risperidone;
b) a biodegradable triblock copolymer having the formula:

poly(lactic acid)$_v$-poly(ethylene glycol)$_w$-poly(lactic acid)$_x$ wherein v and x are the number of repeat units ranging from 24 to 682 and w is the number of repeat units ranging from 4 to 273 and v=x or v≠x;
c) a biodegradable diblock copolymer having the formula:

methoxy poly(ethylene glycol)$_y$-poly(lactic acid)$_z$, wherein y and z are the number of repeat units, wherein y is the number of repeat units ranging from 3 to 45 and z is the number of units ranging from 7 to 327; and wherein the ratio of the biodegradable triblock copolymer of (b) and the biodegradable diblock copolymer of (c) is 1:3 to 1:8 or 1:1 to 1:19 or 3:2 to 1:19, in said formulation, which is insoluble in an aqueous environment, for use in treating a psychiatric disease or disorder.

* * * * *

UNITED STATES PATENT AND TRADEMARK OFFICE
CERTIFICATE OF CORRECTION

PATENT NO. : 12,383,493 B2
APPLICATION NO. : 17/642410
DATED : August 12, 2025
INVENTOR(S) : Anthony Rech et al.

Page 1 of 1

It is certified that error appears in the above-identified patent and that said Letters Patent is hereby corrected as shown below:

In the Claims

Column 23; Lines 28-30, Claim 20:
Change:
"20. The method of claim 13, wherein the cumulative release is determined by in vitro release (IVR) method disclosed herein."

To:
--20. The method of claim 16, wherein the cumulative release is determined by in vitro release (IVR) method disclosed herein.--

Signed and Sealed this
Twenty-first Day of October, 2025

John A. Squires
*Director of the United States Patent and Trademark Office*